(12) United States Patent
Perschbacher et al.

(10) Patent No.: US 7,376,461 B2
(45) Date of Patent: May 20, 2008

(54) DYNAMIC MODE SWITCH FOR EARLY DETECTION OF TACHYARRHYTHMIA

(75) Inventors: David L. Perschbacher, Coon Rapids, MN (US); Kenneth L. Baker, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 438 days.

(21) Appl. No.: 10/274,697

(22) Filed: Oct. 18, 2002

(65) Prior Publication Data

US 2004/0077963 A1   Apr. 22, 2004

(51) Int. Cl.
*A61N 1/365* (2006.01)
(52) U.S. Cl. ........................................ 607/14
(58) Field of Classification Search ............. 607/4, 607/5, 9, 14, 25, 13, 15
See application file for complete search history.

(56) References Cited

U.S. PATENT DOCUMENTS

| | | | |
|---|---|---|---|
| 4,712,556 A * | 12/1987 | Baker, Jr. ............... | 607/14 |
| 4,860,749 A | 8/1989 | Lehmann | |
| 4,944,298 A * | 7/1990 | Sholder ............... | 607/14 |
| 5,653,738 A * | 8/1997 | Sholder ............... | 607/14 |
| 5,893,882 A * | 4/1999 | Peterson et al. ......... | 607/14 |
| 6,128,533 A | 10/2000 | Florio et al. | |
| 6,411,847 B1 | 6/2002 | Mower | |
| 6,484,058 B1 | 11/2002 | Williams et al. | |
| 2001/0014817 A1 * | 8/2001 | Armstrong et al. ......... | 607/14 |

* cited by examiner

*Primary Examiner*—George R. Evanisko
*Assistant Examiner*—Michael Kahelin
(74) *Attorney, Agent, or Firm*—Schwegman, Lundberg & Woessner, P.A.

(57) ABSTRACT

An algorithm executed in an implantable cardiac rhythm management device (CRMD) automatically adjusts the time that an atrial pace (AP) and/or a ventricular pace (VP) pulse is generated by a pulse generator when the expected time of occurrence of the AP pulse falls within a predetermined interval referred to as the "lowest tachy zone". By delaying the generation of the AP pulse until outside of the lowest tachy zone, undersensing of ventricular tachycardia depolarizations due to cross-channel refractory and VP refractory is avoided.

4 Claims, 6 Drawing Sheets

DYNAMIC MODE SWITCH FOR EARLY DETECTION OF TACHYARRHYTHMIA

BACKGROUND OF THE INVENTION

I. Field of the Invention

This invention relates generally to cardiac rhythm management devices, and more particularly to a method and apparatus for avoiding undersensing of episodes of tachycardia due to brady/tachy crossover in the device.

II. Discussion of the Prior Art

Many rate enhancements found in state-of-art multichamber pacemakers and pacemaker/defibrillators may cause the device to pace the heart at rates in the excess of a programmed Lower Rate Limit (LRL). For example, features now commonly found in CRMDs, such as rate smoothing, rate adaption, ventricular rate regulation, etc., may cause the device to generate pace pulses faster than the programmed LRL and as fast as a programmed Upper Rate Limit (URL). For devices that detect and/or treat tachyarrhythmias, it often happens that the heart rate due to the tachycardia episode and the programmed URL share a common range of heart rate. That is, at rates near or at the URL, the atrial pace can be inside the lowest tachy zone (LTZ) as a condition referred to as "brady/tachy cross-over".

For situations of brady/tachy crossover, if the CRMD is pacing the heart at a fast rate when a ventricular tachyarrhythmia occurs, then detection and possible treatment of the tachyarrhythmia is often delayed or sometimes completely inhibited due to undersensing of the tachyarrhythmia caused by ventricular sense channel refractory periods initiated by atrial pacing.

In accordance with the present invention, a pacing mode switch algorithm is implemented in the software/firmware of the microprocessor-based controller used in implementing the CRMD that addresses incidences of brady/tachy crossover whereby undersensing of the tachyarrhythmia due to ventricular sensed channel refractory periods initiated by atrial pacing is avoided. The algorithm operates such that whenever the device is scheduled to deliver an atrial pace pulse at an interval relative to the previous ventricular sense or pace that is shorter than the longest known interval of the tachyarrhythmia, the device delays generation of the atrial pace pulse. The next scheduled ventricular pace pulse would still be delivered so long as it is not inhibited by a ventricular sensed event.

The mode switch is only applied on those cardiac cycles where the V-to-A pace interval is shorter than a programmed ventricular tachycardia interval referred to as the "lowest tachy zone". The algorithm of the present invention also helps reduce undersensing of atrial arrhythmias due to atrial sensed channel refractory periods that are initiated by atrial pacing, although it will not eliminate that phenomenon entirely.

SUMMARY OF THE INVENTION

The present invention comprises an algorithm implemented in the microprocessor-based controller of a CRMD that is capable of detecting tachyarrhythmias so that undersensing of ventricular tachycardia due to brady/tachy crossover is avoided. The CRMD is programmed to establish a predetermined lowest tachy zone, a time interval defining a sensed ventricular rate indicative of a tachycardia episode. The expected time of occurrence of an atrial pace pulse from the device is determined and the generation of the atrial pace pulse is delayed until a time after the lowest tachy zone interval elapses if the calculated expected time of occurrence of the atrial paced pulse occurs within the lowest tachy zone.

The invention is implemented in an implantable, multi-chamber, cardiac rhythm management device that comprises a means for sensing atrial depolarizations in at least one atrial chamber and a means for sensing ventricular depolarizations in at least one ventricular chamber and having a pulse generator for generating atrial pace pulses and ventricular pace pulses. A microprocessor-based controller is adapted to receive signals due to the atrial depolarizations and ventricular depolarizations and provides control signals to the pulse generator for controlling the times at which the atrial pace pulses and ventricular pace pulses are generated. The microprocessor-based controller is programmed to identify ventricular depolarizations as a tachyarrhythmia episode when an interval between ventricular depolarizations is less than a predetermined lowest tachy zone. The microprocessor-based controller is further programmed to delay generation of atrial pace pulses when an expected time of occurrence of the atrial pace pulse falls within the lowest tachy zone whereby undersensing of ventricular depolarization signals due to brady/tachy crossover is avoided.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
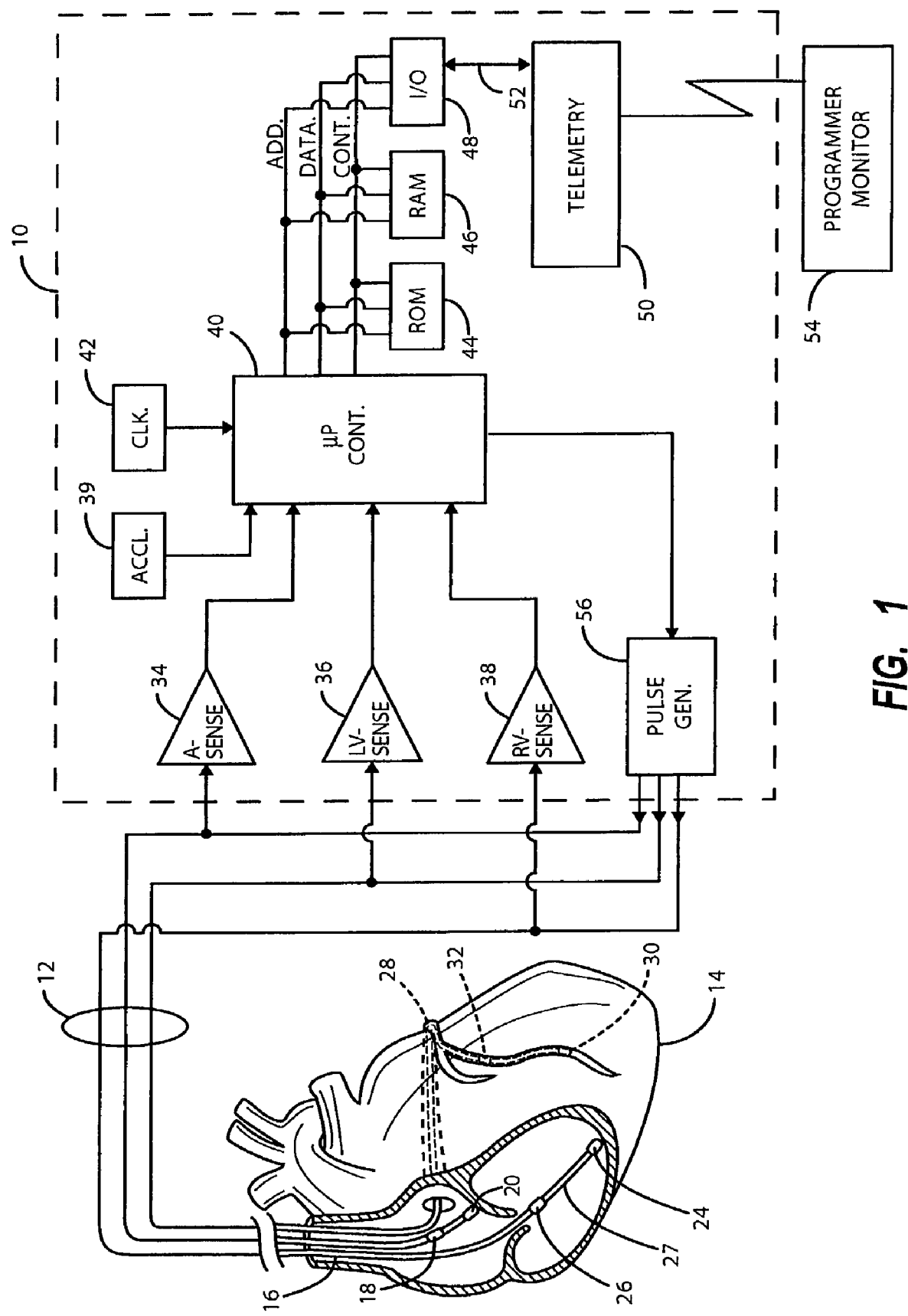
FIG. 1 is a schematic block diagram representation of an implantable CRMD in which the present invention is implemented.

Referring first to FIG. 1, there is illustrated by means of a schematic block diagram a conventional hardware platform in which the present invention can be implemented. Shown enclosed by the broken line box 10 is an implantable cardiac rhythm management device (CRMD) that is connected by means of one or more medical leads 12 to the heart 14. A first lead 16 has an atrial electrode 20 thereon. A ventricular lead 27 has a distal tip electrode 24 and a proximally located ring electrode 26 placed in the right ventricle (RV). A further lead 28 is adapted to be routed through the coronary sinus of the heart and from there down a selected vein on the left side of the heart so that electrodes 30 and 32 are positioned to sense depolarization of the left ventricle.

Signals picked up by the electrode 20 are applied to an atrial sense amplifier 34 forming a part of the device 10. Likewise, the signals from the left ventricular lead 28 are applied to a sense amplifier 36 in the cardiac stimulating device 10. Conductors in the lead 16 connect to the electrodes 24 and 26 and carry signals relating to depolarization of the right ventricle to a right ventricular sense amplifier 38 in the device 10.

As those skilled in the art appreciate, the sense amplifiers 34, 36 and 38 include signal processing circuitry for amplifying and shaping analog signals picked up by the electrodes in and on the heart and these analog signals are applied to an analog-to-digital converter (not shown) forming a part of a microprocessor-based controller 40. In a rate adaptive CRMD, a physiologic sensor, such as accelerometer 39, is also provided. A crystal controlled clock 42 provides timing signals to the microprocessor-based controller. Also coupled to the microprocessor-based controller 40 by an address bus (ADD), a data bus (DATA), and control bus (CONT) are a read-only memory (ROM) 44, a random access memory (RAM) 46 and an input/output interface (I/O) 48. A telemetry circuit 50 is coupled to the I/O circuit 48 by a bi-directional bus 52 and functions to allow a two-way communication with an external programmer/monitor 54.

Stored in the ROM memory 44 is a program executable by the microprocessor contained in the microprocessor-based controller 40 which then functions to control a pulse generator 56 causing it to issue cardiac stimulating pulses over the leads 16 and 28 to initiate depolarization of the right atrium, the right ventricle and the left ventricle at times determined by the microprocessor-based controller 40.

Using the external programmer 54 and the telemetry capabilities of the device 10, a medical professional can program into the device 10 various operating parameters via the RAM memory 46.

Present day dual-chamber pacemakers allow programming of pacing modes, lower rate limits, pulse width, pulse amplitude, sensitivity, refractory periods, maximum tracking rate, AV delay and other parameters. Among pacemaker patients who are chronotropically incompetent (i.e., unable to increase sinus node rate appropriately with exercise), rate-responsive pacemakers allow for increases in pacing rates with exercise. The challenge of appropriately adjusting a response to exercise of these devices in individual patients is becoming increasingly recognized. To facilitate optimal programming of rate-response capability, recently introduced CRMDs incorporate procedures for initial programming of rate-response parameters, subsequent automatic adjustment of these parameters, and retrievable diagnostic data, via the telemetry link, to assess the appropriateness of the rate response. Rate-responsive pacemakers require programmable features to regulate the relation between a sensor output and pacing rate and to limit the maximum sensor-driven pacing rate, i.e., the URL. These programmable parameters must be individually adjusted for each patient, and the choice of one programmable parameter will often depend on the availability of another parameter. For example, in a patient with complete AV block and paroxysmal atrial fibrillation, a dual-chamber pacemaker not having a mode-switching capability most appropriately would be programmed to its DDIR mode, whereas in the same patient, a pacemaker with mode-switching capability most appropriately would be programmed to its DDDR mode with mode switching.

When non-physiological atrial tachyarrhythmias, such as atrial fibrillation or flutter, occur paroxysmally in a patient with a dual-chamber pacemaker programmed to conventional DDD or DDDR mode, the tachyarrhythmia will generally be tracked near the programmed maximum tracking rate (MTR), leading to an undesirable acceleration of ventricular pacing rate. Newer dual-chamber devices incorporate algorithms for detecting rapid, non-physiological atrial rates and automatically switch modes to one that does not track atrial activity, such as DDI or DDIR. When the atrial tachyarrhythmia terminates, the pacemaker automatically reverts back to its DDD or DDDR mode.

Figure 2:
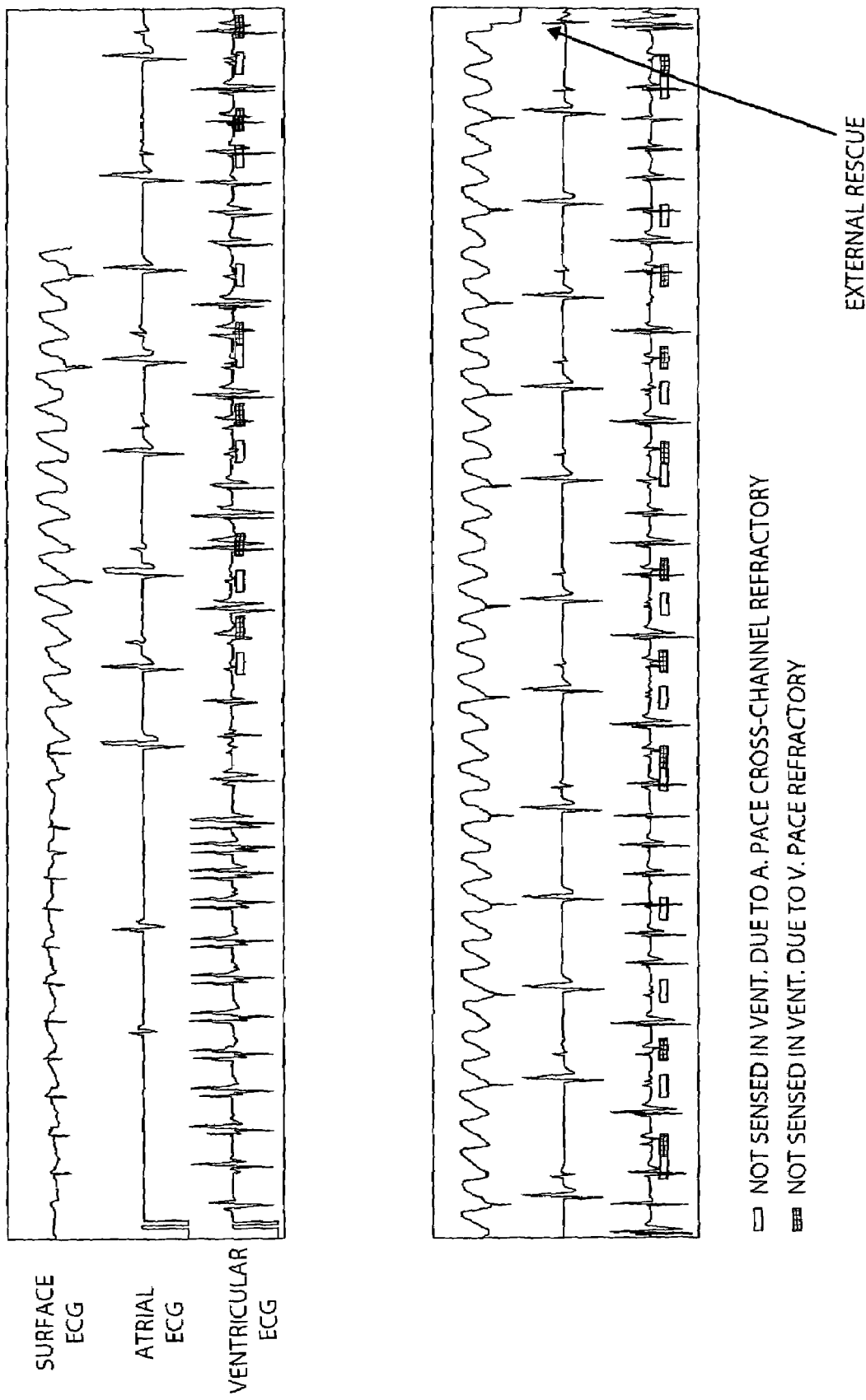
FIG. 2 is a strip recording of an episode of induced ventricular tachycardia showing undersensing of ventricular beats due to brady/tachy cross-over.

Referring to FIG. 2, the uppermost waveform comprises a surface ECG aligned time-wise with an atrial electrogram (middle waveform) and a ventricular electrogram (bottom waveform) where the subject has had an episode of ventricular tachycardia induced. The electrogram signals are developed by the CRMD. A pacemaker operating in the DDI mode with a LRL of 50 beats-per-minute and a URL of 120 beats-per-minute and with a fixed AV delay of 300 ms and rate smoothing down 12% and up 9% produce the atrial and ventricular electrograms illustrated. It can be seen from this waveform that by initially pacing the subject at a high rate of about 220 beats-per-minute, an episode of ventricular tachycardia or flutter has been induced, represented by the somewhat sinusoidal-shaped waves in the surface EKG. The lower waveform has been annotated to reflect where ventricular beats were under-sensed due to A-pace cross-channel refractory and V-pace refractory conditions. Those beats that were not sensed due to A-pace cross-channel refractory are underlined with a solid bar and those not sensed due to V-pace refractory are underlined with an open bar. It is readily apparent that due to brady/tachy cross-over, numerous ventricular beats have gone undetected.

Figure 3:
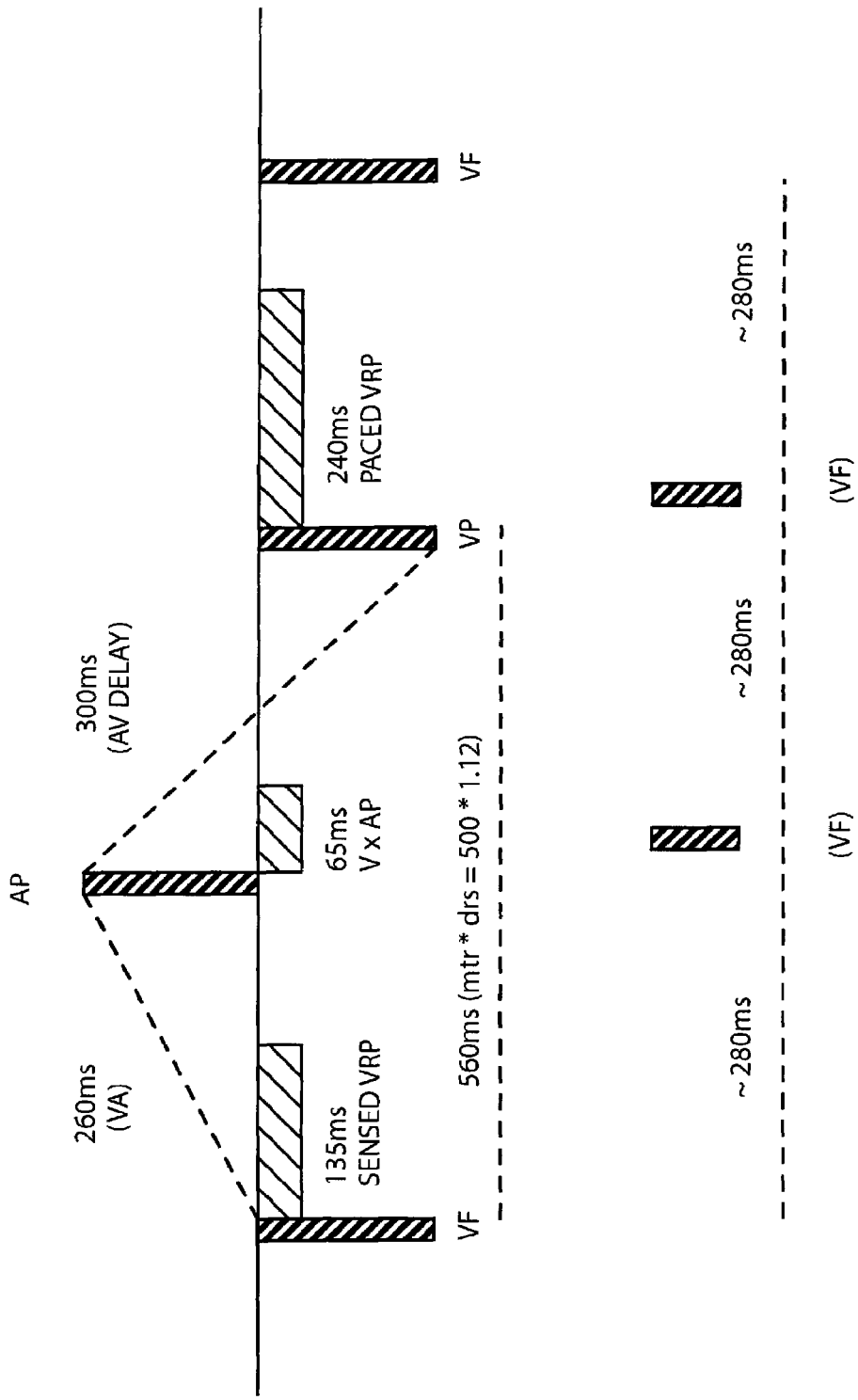
FIG. 3 is a diagram illustrating how timing cycles are set up in a pacemaker or pacemaker/defibrillator and illustrating undersensing occasioned by atrial refractory periods and ventricular refractory periods.

Referring now to FIG. 3, there is illustrated the manner in which timing cycles are set up in a multi-chamber pacemaker or pacemaker/defibrillator and illustrating under-sensing because of the presence of atrial refractory periods and ventricular refractory periods in the timing cycle. Starting with a first ventricular beat VF, which stands for a ventricular fib beat, a time is established when the next ventricular pace (VP) beat will be delivered by the pacemaker. In the case illustrated, this time interval is determined by programmable variables including the "maximum tracking rate" MTR and the "down-rate smooth limit" (drs). These two factors are multiplied and with a MTR of 500 and a drs of 1.12, the time interval from the sensed beat VF to the next paced beat (VP) is 560 milliseconds.

The AV delay value, here 300 ms, is a parameter programmed in by the physician and this establishes the time of occurrence of the A-pace (AP) pulse produced by the implantable device. The diagram of FIG. 3 also shows that following the occurrence of a sensed ventricular beat, there is a fixed refractory interval of 135 ms. Likewise, following the occurrence of an A-pace signal, a preprogrammed atrial refractory period (here 65 ms) is provided. Finally, following a paced ventricular beat (VP), there is a ventricular refractory period whose length is also a programmable quantity, here set at 240 ms.

Referring again to FIG. 2, it will be seen that the ventricular tachycardia is at an interval of about 280 ms, which therefore causes the ventricular fibrillation beats (VF) to fall within the atrial refractory period and the paced ventricular refractory period. Hence, those beats are not sensed by the sense amplifiers 34, 36 or 38, which are purposely disabled at these times.

From what has been explained with the aid of FIGS. 2 and 3, if the device is pacing the heart at a rate approaching the URL and a ventricular tachyarrhythmia occurs, the detection and possible treatment of the tachyarrhythmia is frequently delayed or completely inhibited due to undersensing because of ventricular sense channel refractory periods that have been initiated by atrial pacing. The methodology or algorithm implemented in the conventional implantable device of FIG. 1 for enhancing detection of ventricular depolarizations during brady/tachy cross-over will now be explained with the aid of the diagrams of FIGS. 4, 5A and 5B.

Figure 4:
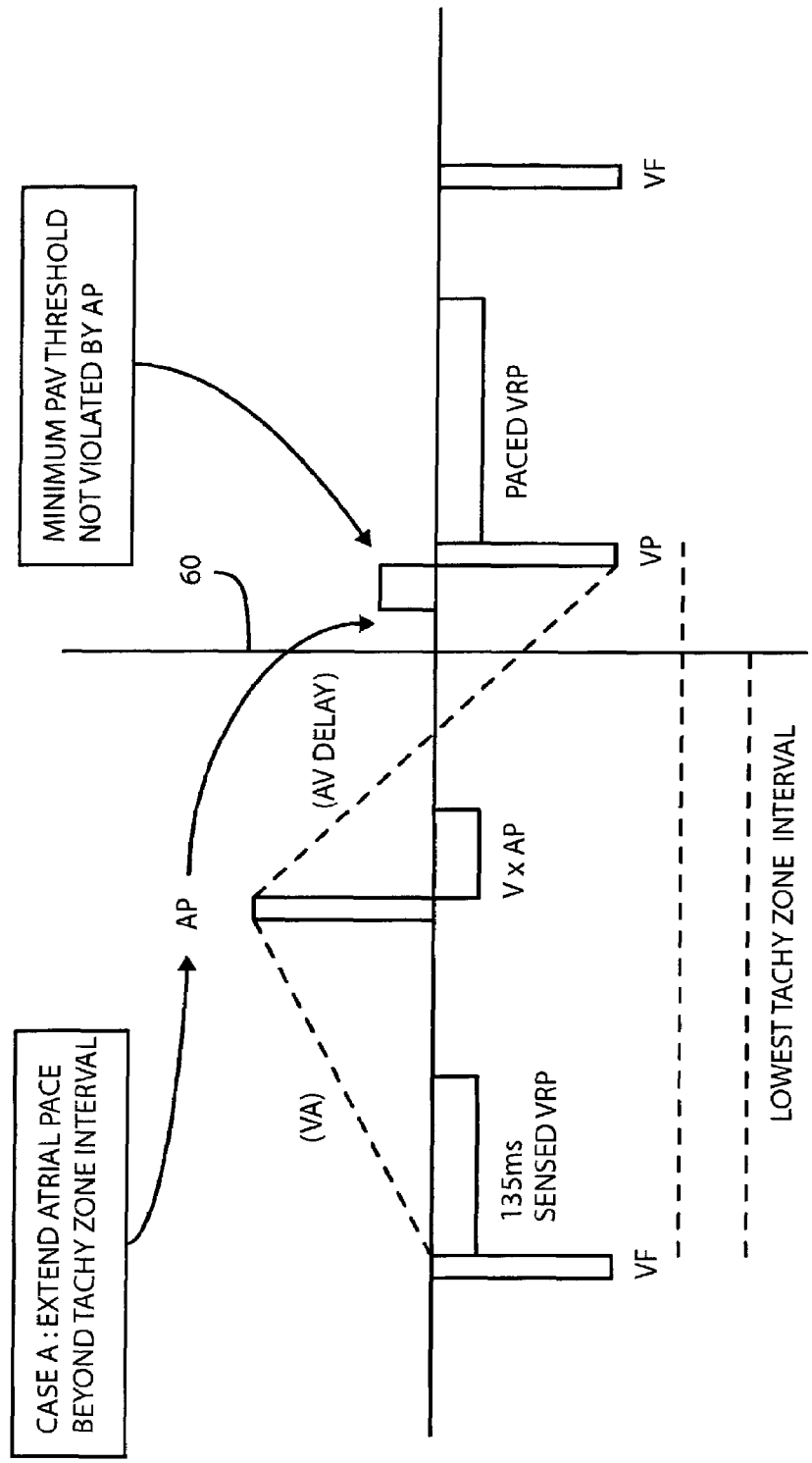
FIG. 4 is a diagram helpful in explaining the mode switch algorithm when an atrial pace is scheduled to occur in the lowest tachy zone.

The timing diagram of FIG. 4 includes a long vertical line 60 marking the end of a programmed interval, referred to as the "lowest tachy zone interval", which defines the longest interval (slowest rate) that sensed beats can have and be classified as a tachycardia. This parameter varies from patient-to-patient and is arrived at by observing ECG data for the patient over a period of time. Any ventricular beats which are occurring at a rate that makes the interval between beats shorter than the lowest tachy zone interval are considered to be a tachycardia episode. The interval between the occurrence of an atrial pace (AP) and the line 60 is a zone in which under-sensing can occur due to the atrial cross-channel refractory period that follows the AP pulse.

The mode switch algorithm of the present invention operates to determine the expected time of occurrence of an A-pace pulse and to postpone or delay the generation of the AP so that it occurs outside the lowest tachy zone. In the event that the resulting AV delay is rendered too short to be physiologically beneficial, the algorithm executed by the CRMD is executed as a two-step process illustrated graphically in FIGS. 5A and 5B.

Figure 5A:
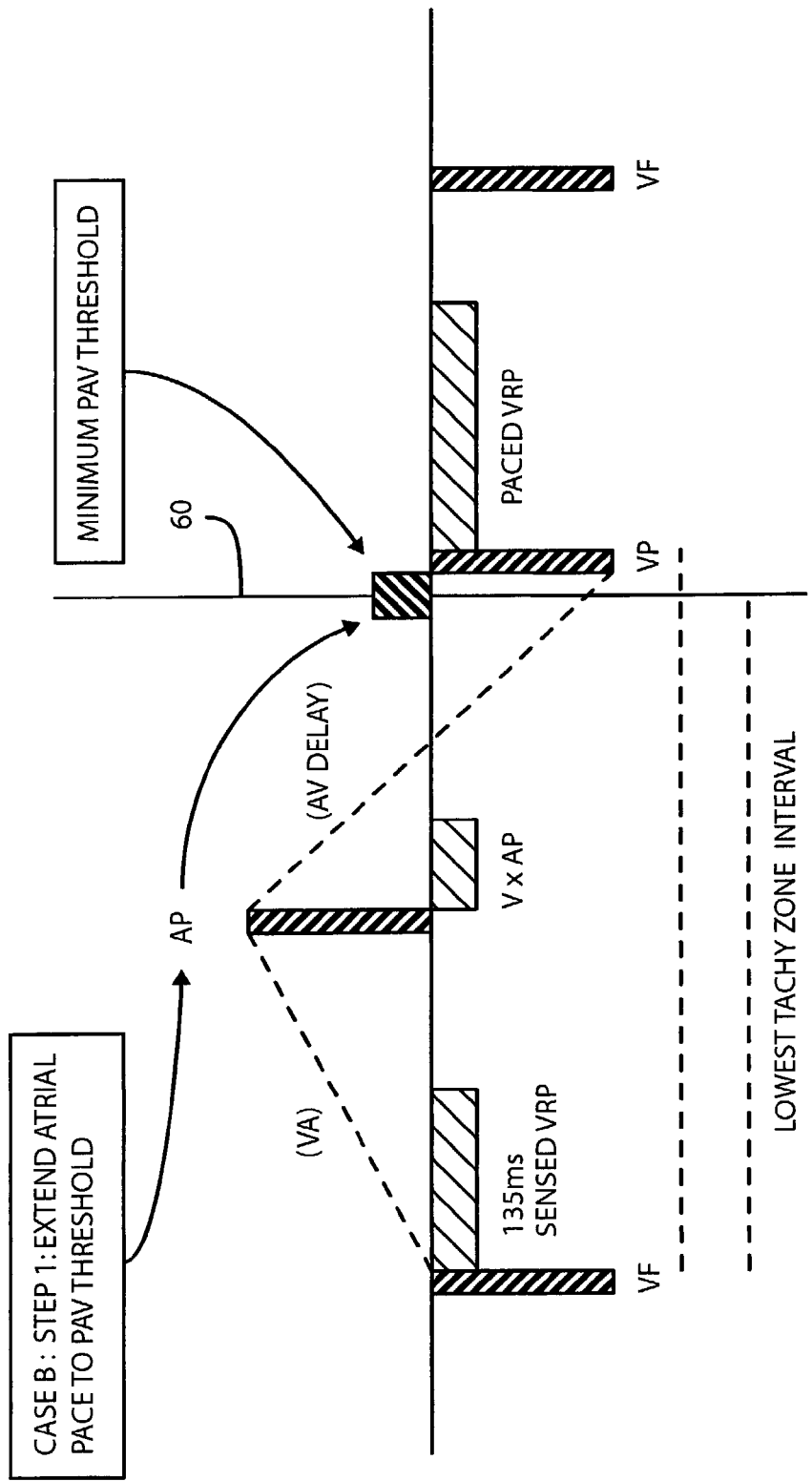
FIGS. 5A and 5B are diagrams helpful in understanding the mode switch algorithm for instances where delaying the atrial pace pulse beyond the end of the lowest tachy zone results in an AV delay that is too short to be physiologically beneficial.
Figure 5B:
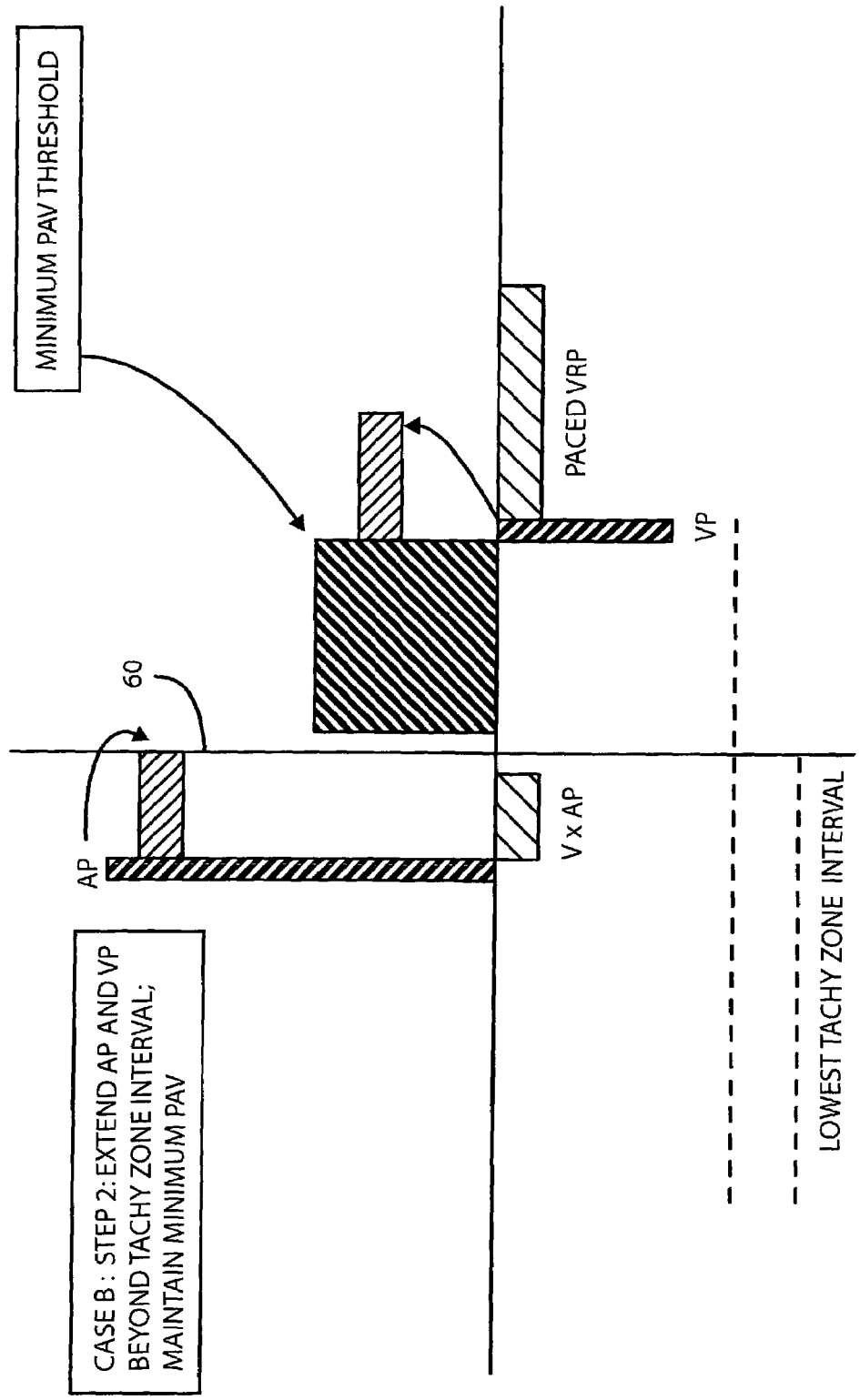

Referring to FIG. 5A, when the expected time of occurrence of the AP pulse falls within the lowest tachy zone, the AP pulse is delayed up to a paced AV delay threshold. Then, in a second step (FIG. 5B), both the AP and the VP are delayed to occur outside of the lowest tachy zone. Both the AP and VP pulses are shifted in time by an equal amount, each falling outside the lowest tachy zone while maintaining a desired AV delay interval between them.

By automatically switching the mode, so that neither AP nor VP fall within the lowest tachy zone, it is insured that neither the cross-channel refractory nor the VP refractory intervals will fall within the lowest tachy zone. Hence, sensing of VT early is enhanced in that sensed VT events cannot fall within a refractory period of the CRMD.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. In a multi-chamber cardiac rhythm management device capable of detecting tachyarrhythmia, a method of avoiding undersensing of ventricular tachycardia due to brady/tachy crossover, the method comprising the steps of:

establishing an upper pacing rate limit interval in the device;

establishing a lowest tachy zone interval in the device, wherein the upper pacing rate limit interval is greater than the lowest tachy rate zone interval;

programming a scheduled first paced AV delay interval in the device between a scheduled atrial pace pulse and a scheduled ventricular pace pulse;

programming a specified fixed minimum paced AV delay interval between an atrial pace pulse and a ventricular pace pulse in the IMD, wherein the specified fixed minimum paced AV delay interval is shorter than the first paced AV delay;

detecting an intrinsic ventricular tachyarrhythmia depolarization, thereby initiating timing of the lowest tachy rate zone interval, and also thereby initiating timing of a ventricular pace pulse interval;

calculating an atrial pace pulse interval to follow the intrinsic ventricular depolarization using the ventricular pace pulse interval less the first paced AV delay interval;

if the calculated atrial pace pulse interval is within the lowest tachy rate zone interval and the ventricular pace pulse interval less the lowest tachy rate zone interval equals or exceeds the specified fixed minimum paced AV delay, then delaying generation of the atrial pace pulse until after expiration of the lowest tachy zone interval by reducing the first paced AV delay, thereby preserving the ventricular pace pulse interval; and if the calculated atrial pace pulse interval is within the lowest tachy rate zone interval and the calculated ventricular pace pulse interval less the lowest tachy rate zone interval is less than the specified fixed minimum paced AV delay, then delaying the atrial pace pulse until after expiration of the lowest tachy rate zone interval and delaying generation of the ventricular pace pulse until after the minimum paced AV delay interval elapses following the delayed atrial pace pulse.

2. An implantable, multichamber cardiac rhythm management device comprising:

(a) means for sensing atrial depolarizations in at least one atrial chamber;

(b) means for sensing ventricular depolarizations in at least one ventricular chamber;

(c) a pulse generator for generating atrial pace pulses and ventricular pace pulses;

(d) a microprocessor-based controller adapted to receive signals due to the atrial depolarizations and ventricular depolarizations and providing control signals to the pulse generator for controlling times at which the atrial pace pulses are generated, the microprocessor-based controller being programmed to establish:

an upper pacing rate limit interval, a lowest tachy zone interval being less than the upper pacing rate limit interval, a scheduled first paced AV delay interval, and a specified fixed minimum paced AV delay interval wherein the specified fixed minimum paced AV delay interval is shorter than the first paced AV delay interval, the microprocessor-based controller being further programmed to:

detect an intrinsic ventricular tachyarrhythmia depolarization, which initiates timing of the lowest tachy rate zone interval, and which also initiates timing of a ventricular pace pulse interval;

calculate an atrial pace pulse interval to follow the intrinsic ventricular depolarization using the ventricular pace pulse interval less the first paced AV delay interval;

if the calculated atrial pace pulse interval ends within the lowest tachy rate zone interval and the ventricular pace pulse interval less the lowest tachy rate zone interval equals or exceeds the specified fixed minimum paced AV delay, then delay generation of the atrial pace pulse until after expiration of said lowest tachy zone interval by reducing the first paced AV delay, to avoid under-sensing of ventricular depolarization signals due to brady-tachy crossover and preserving the ventricular pace pulse interval;

if the calculated atrial pace pulse interval ends within the lowest tachy rate zone interval and the calculated ventricular pace pulse interval less the lowest tachy rate zone interval is less than the specified fixed minimum paced AV delay, then delay the atrial pace pulse until after expiration of the lowest tachy rate zone interval and delay generation of the ventricular pace pulse until after the minimum paced AV delay interval elapses following the delayed atrial pace pulse.

3. The device of claim 2 wherein timing of the ventricular pace pulse interval is determined using a programmed mean tracking rate and a programmed down-rate smooth limit.

4. The device of claim 2 wherein the microprocessor-based controller is further programmed to delay generation of the atrial pace pulse and the ventricular pace pulse by an equal amount if the calculated atrial pace pulse interval ends within the lowest tachy rate zone interval and the calculated ventricular pace pulse interval less the lowest tachy rate zone interval is less than the specified fixed minimum paced AV delay.

* * * * *

UNITED STATES PATENT AND TRADEMARK OFFICE
CERTIFICATE OF CORRECTION

PATENT NO. : 7,376,461 B2 Page 1 of 1
APPLICATION NO. : 10/274697
DATED : May 20, 2008
INVENTOR(S) : Perschbacher et al.

It is certified that error appears in the above-identified patent and that said Letters Patent is hereby corrected as shown below:

In column 5, line 66, in Claim 1, delete "progranmiing" and insert -- programming --, therefor.

Signed and Sealed this

Twenty-ninth Day of July, 2008

JON W. DUDAS
*Director of the United States Patent and Trademark Office*